(12) United States Patent
Akechi et al.

(10) Patent No.: US 8,557,597 B2
(45) Date of Patent: Oct. 15, 2013

(54) TOTAL ORGANIC CARBON MEASURING INSTRUMENT

(75) Inventors: Masakazu Akechi, Kyoto (JP); Hirohisa Abe, Kyoto (JP); Yoichi Fujiyama, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 13/345,032

(22) Filed: Jan. 6, 2012

(65) Prior Publication Data

US 2012/0107947 A1 May 3, 2012

Related U.S. Application Data

(62) Division of application No. 12/532,146, filed as application No. PCT/JP2007/055653 on Mar. 20, 2007, now abandoned.

(51) Int. Cl.
*G01N 33/00* (2006.01)
*G01N 25/08* (2006.01)
*G01N 1/10* (2006.01)
*G01N 31/12* (2006.01)

(52) U.S. Cl.
USPC ............. 436/146; 436/150; 436/180; 422/78

(58) Field of Classification Search
USPC ........................................ 436/146; 422/78
See application file for complete search history.

(56) References Cited

U.S. PATENT DOCUMENTS

| | | | |
|---|---|---|---|
| 5,132,094 A | 7/1992 | Godec et al. | |
| 5,171,694 A | 12/1992 | Connolly | |
| 6,444,474 B1 | 9/2002 | Thomas et al. | |
| 6,723,565 B2 * | 4/2004 | Davenport et al. | 436/133 |
| 6,737,276 B1 * | 5/2004 | Voss et al. | 436/146 |
| 7,931,865 B2 | 4/2011 | Fujiyama et al. | |
| 2003/0211626 A1 | 11/2003 | Davenport et al. | |
| 2010/0098588 A1 | 4/2010 | Fujiyama et al. | |

FOREIGN PATENT DOCUMENTS

| | | |
|---|---|---|
| JP | 2510368 B2 | 6/1996 |
| JP | 2001-281189 A | 10/2001 |
| JP | 2005-106668 A | 4/2005 |
| JP | 2006-90732 A | 4/2006 |
| JP | 2006-300633 A | 11/2006 |

(Continued)

OTHER PUBLICATIONS

Machine translation of JP-2006300633-A.*

(Continued)

*Primary Examiner* — Jill Warden
*Assistant Examiner* — Charles D Hammond
(74) *Attorney, Agent, or Firm* — Cheng Law Group, PLLC

(57) ABSTRACT

A total organic carbon measuring instrument including a measuring unit composed of, integrated together, organic substance oxidation part and carbon dioxide separation part and conductivity measuring part, control unit and data processing unit. In order to enhance the accuracy of conductivity measurement, the control unit is constructed so as to stop feeding of a sample water at the time of oxidation of organic substance and carry out feeding of the sample water at the time of sample water moving to the organic substance oxidation decomposition part and carbon dioxide separation part. The data processing unit is constructed so as to measure the total organic carbon concentration on the basis of conductivity at the time of arriving of sample water irradiated with ultraviolet rays of which relative intensity is a given value or higher at the carbon dioxide separation part.

8 Claims, 6 Drawing Sheets

(56) References Cited

FOREIGN PATENT DOCUMENTS

| JP | 2006-337032 A | 12/2006 |
|---|---|---|
| WO | WO-91/13362 A1 | 9/1991 |
| WO | WO-2006/126296 A1 | 11/2006 |

OTHER PUBLICATIONS

Machine Translation of JP-2006300633-A. Nov. 2, 2006.*
International Search Report for the Application No. PCT/JP2007/055653 mailed Jun. 19, 2007.

* cited by examiner

TOTAL ORGANIC CARBON MEASURING INSTRUMENT

CROSS REFERENCE TO RELATED APPLICATIONS

This application is a Divisional Application of patent application Ser. No. 12/532,146, filed Sep. 18, 2009 now abandoned which is a 371 application of application Ser. No. PCT/JP2007/055653, filed on Mar. 20, 2007, the entire contents of which are hereby incorporated by reference.

TECHNICAL FIELD

The present invention relates to a total organic carbon measuring instrument (hereinafter, also referred to as a "TOC measuring instrument") for measuring the total organic carbon (TOC) content of a water sample. More particularly, the present invention relates to a μTAS (Micro Total Analysis System) obtained by integrating some functions necessary for measuring the TOC content of low-impurity water called "pure water" or "ultra-pure water" such as separation of organic substances by a carbon dioxide separation part and measurement of conductivity by a conductivity measuring part.

BACKGROUND ART

The amount of organic substances contained in low-impurity water such as water for pharmaceutical production, process water for semiconductor manufacturing, cooling water, boiler water, or tap water is monitored by measuring the TOC content of a water sample.

Examples of a total organic carbon measuring method include a combustion oxidation method in which organic substances are oxidized by combustion in a high-temperature furnace and a wet oxidation method in which organic substances are chemically oxidized using UV light and oxidants. In the case of TOC measurements of pure water and ultra-pure water requiring high sensitivity, the latter, that is, a wet oxidation method is generally used.

As a method for measuring TOC by wet oxidation, there is a method including the steps of: converting organic substances contained in a water sample to carbon dioxide by an oxidation reactor; transferring the carbon dioxide into measurement water through a gas-permeable membrane; and feeding the measurement water containing the carbon dioxide transferred from the water sample to a conductivity measuring unit to measure the conductivity of the measurement water to detect the concentration of carbon dioxide (see Patent Documents 1 and 2).

Further, as conductivity measurement of carbon dioxide, there is also a method of measuring TOC of an organic compound in which at least two electrodes are provided at positions before and after oxidation, and a difference in the conductivity of the water sample between before and after oxidation is detected (see Patent Document 3).

As a method for measuring the TOC content of low-impurity water such as process water for semiconductor manufacturing or water for pharmaceutical production, there is a method in which organic substances contained in a water sample are decomposed by UV light to carbon dioxide, the carbon dioxide is transferred into measurement water through a carbon dioxide separation part, and the conductivity of the measurement water is measured. Such a method is known as a method capable of measuring the TOC content of low-impurity water with high accuracy using a relatively compact instrument.

The present inventors have already developed a total organic carbon measuring instrument obtained by integrating some devices using a microfabrication technique to suggest a reduction in the volume of water to be measured as compared to conventional measuring instruments (see Patent Document 4). This TOC measuring instrument is intended to achieve both a reduction in the consumption of a water sample and a reduction in the influence of elution of piping materials and/or the influence of carbon dioxide to be transferred.

Patent Document 1: Japanese Patent No. 2510368
Patent Document 2: Japanese Patent Application Laid-open No. 2006-90732
Patent Document 3: Japanese Patent Application Laid-open No. 2001-281189
Patent Document 4: Japanese Patent Application Laid-open No. 2006-300633

DISCLOSURE OF THE INVENTION

Problem to be Solved by the Invention

In the case of using such a total organic carbon measuring instrument obtained by integrating some devices, it is necessary to stop the feeding of a water sample during irradiation with UV light to sufficiently oxidize organic substances. However, since the intensity distribution of UV light emitted from a UV lamp is not uniform, the organic substances contained in the water sample are not uniformly oxidized in a flow channel of an organic substance oxidation part. In this case, although carbon dioxide is generated by oxidation of the organic substances, the concentration of carbon dioxide in the water sample is low in part of the flow channel not sufficiently irradiated with UV light, and therefore, there is a problem that the concentration of TOC of the water sample becomes lower than its true value because the conductivity of measurement water is not sufficiently increased even after the water sample arrives at the carbon dioxide separation part.

Therefore, it is an object of the present invention to provide a total organic carbon measuring instrument capable of enhancing the accuracy of conductivity measurement.

Means for Solving the Problem

The present invention is directed to a total organic carbon measuring instrument including a measuring unit, a control unit for controlling the operation of liquid delivery in the measuring unit, and a data processing unit for determining the concentration of total organic carbon from the conductivity of measurement water. The measuring unit has an organic substance oxidation part for oxidizing organic substances contained in a supplied water sample to carbon dioxide by irradiation with UV light, a carbon dioxide separation part having a water sample channel through which a water sample transferred from the organic substance oxidation part flows and a measurement water channel through which measurement water constituted from deionized water flows, the carbon dioxide separation part being formed by integrating the water sample channel and the measurement water channel being in contact with each other gas-permeably and laminated in this order from top to bottom, and a conductivity measuring part for measuring a conductivity of measurement water transferred from the carbon dioxide separation part. The measuring unit is formed by laminating the organic substance oxidation part, the carbon dioxide separation part, and the conductivity measuring part in this order from top to bottom.

The control unit stops feeding the water sample during oxidation of organic substances and performs feeding the water sample when the water sample is moved to the carbon dioxide separation part through the organic substance oxidation part. The data processing unit determines the concentration of total organic carbon based on conductivity measured when the water sample irradiated with UV light of which relative intensity is equal to or higher than a certain value is flowing through the carbon dioxide separation unit.

When organic substances contained in a water sample are decomposed by UV light, there is a case where gas components other than carbon dioxide are generated from compounds contained in the water sample and having elements other than carbon such as nitrogen compounds, and are then transferred into measurement water together with carbon dioxide, thereby adversely affecting conductivity measurement.

The carbon dioxide separation part may have, between the water sample channel and the measurement water channel, an intermediate water channel in which intermediate water having a pH higher than that of a water sample flowing through the water sample channel but within a neutral range is present. In this case, the water sample channel and the intermediate water channel are in contact with each other with a gas-permeable membrane being interposed therebetween, and the intermediate water channel and the measurement water channel are in contact with each other with a gas-permeable membrane being interposed therebetween. Further the water sample channel, the intermediate water channel, and the measurement water channel are laminated in this order from top to bottom and integrated.

Generally, in the case of determining the TOC content of a water sample based on the conductivity of measurement water measured using a TOC measuring instrument having a carbon dioxide separation part, the water sample is made strongly acidic by adding an acid to the water sample in order to remove original dissolved carbon dioxide, promote the transfer of gas components into the water sample, and stabilize measurement. When a water sample containing nitrogen compounds such as urea and the like is irradiated with UV light under strongly acidic conditions, the nitrogen compounds are oxidatively decomposed so that nitric acid and nitrous acid are generated.

As shown in FIG. 6, the ratio between nitrous acid and nitrite ion present in water varies depending on pH. More specifically, nitrous acid is present as a gas component under acidic conditions but present as nitrite ion under neutral to alkaline conditions.

In the case of a conventional TOC measuring instrument having a carbon dioxide separation part in which a gas-permeable membrane is interposed between an acidic water sample and neutral measurement water, nitrous acid generated in the water sample is transferred through the gas-permeable membrane into the measurement water and is then present as nitrite ion. As a result, nitrous acid causes positive interference in conductivity measurement, that is, the conductivity of the measurement water becomes high.

However, in the case of the TOC measuring instrument according to the present invention, by providing, between the water sample channel and the measurement water channel, an intermediate water channel in which the intermediate water having a pH higher than that of a water sample flowing through the water sample channel but within a neutral range is present, it is possible to suppress the transfer of nitrous acid into measurement water. This is due to the following reasons.

Nitrous acid generated in a water sample is transferred into the intermediate water channel through the gas-permeable membrane. However, the ratio of nitrous acid present as a gas component in the intermediate water is decreased by maintaining the pH of the intermediate water around neutral, and then nitrous acid in the intermediate water is present as nitrite ion which cannot pass through the gas-permeable membrane.

In a case where the intermediate water and the measurement water are both, for example, deionized water, the pH of each of the intermediate water and the measurement water is maintained at 5 to 7 by dissolved carbonic acid. Under such conditions, the carbonic acid component is mostly present as a gas component, but nitrous acid is mostly present as an ion component. The rate of gas transfer from the intermediate water to the measurement water is determined by the difference in gas concentration between them, and therefore, the transfer rate of nitrous acid is lower than that of carbonic acid because nitrous acid is mostly present as ion. By appropriately designing the thickness of the gas-permeable membrane interposed between the intermediate water and the measurement water, the area of contact between the gas-permeable membrane and the intermediate water and the area of contact between the gas-permeable membrane and the measurement water based on the difference in transfer rate between carbonic acid and nitrous acid, it is possible to reduce the influence of nitrous acid on carbon dioxide.

By providing such an intermediate water channel, it is possible to achieve both a high transfer rate of carbon dioxide and a reduction in the influence of interfering substances. Nitrous acid is exemplified as an interfering substance, but the influence of other interfering substances can be diminished as long as they are present in a gaseous state under acidic conditions but are ionized under neutral to alkaline conditions.

Further, even when the TOC measuring instrument according to the present invention has a multiple structure due to providing the intermediate water channel so that it becomes difficult to keep the flow rate ratio among a water sample, intermediate water, and measurement water, and the timing of liquid delivery constant, the TOC content of a water sample can be accurately determined because the water sample is sufficiently oxidized and is then allowed to flow through the carbon dioxide separation part.

An example of the organic substance oxidation part of the total organic carbon measuring instrument according to the present invention includes one having a flow channel through which a water sample flows and a UV light incident portion for allowing the water sample flowing through the flow channel to be irradiated with UV light. Such an organic substance oxidation part using UV light can be reduced in size and easily integrated with other parts because it does not need a heating portion or a pressuring portion. The flow channel of the organic substance oxidation part through which the water sample flows may meander in the UV light incident portion to have an increased flow channel length. This makes it possible to increase the time for UV light irradiation to enhance oxidation efficiency.

In order to increase the time during when the water sample remains in contact with the intermediate water in the carbon dioxide separation part to enhance the efficiency of gas transfer from the water sample into the intermediate water, part of the water sample channel being in contact with the gas-permeable membrane may meander to have an increased flow channel length.

In order to increase the time when the measurement water remains in contact with the intermediate water in the carbon dioxide separation part to enhance the efficiency of gas transfer from the intermediate water into the measurement water, part of the measurement water channel being in contact with the gas-permeable membrane may meander to have an increased flow channel length.

Further, in order to increase the retention time of the intermediate water in the intermediate water channel, part of the intermediate water channel being in contact with the gas-permeable membranes may meander to have an increased flow channel length.

It is important for the intermediate water to set its pH. Examples of intermediate water include, in addition to pure water or deionized water, a buffer solution having a pH within a neutral range.

Effects of the Invention

According to the present invention, as described above, since the control unit stops feeding the water sample during oxidation of organic substances and performs feeding the water sample when the water sample is moved to the carbon dioxide separation part through the organic substance oxidation part, and the data processing unit determines the concentration of total organic carbon based on conductivity measured when a water sample irradiated with UV light of which relative intensity is equal to or higher than a certain value is flowing through the carbon dioxide separation unit, it is possible to accurately measure the TOC value of the water sample.

Figure 1:
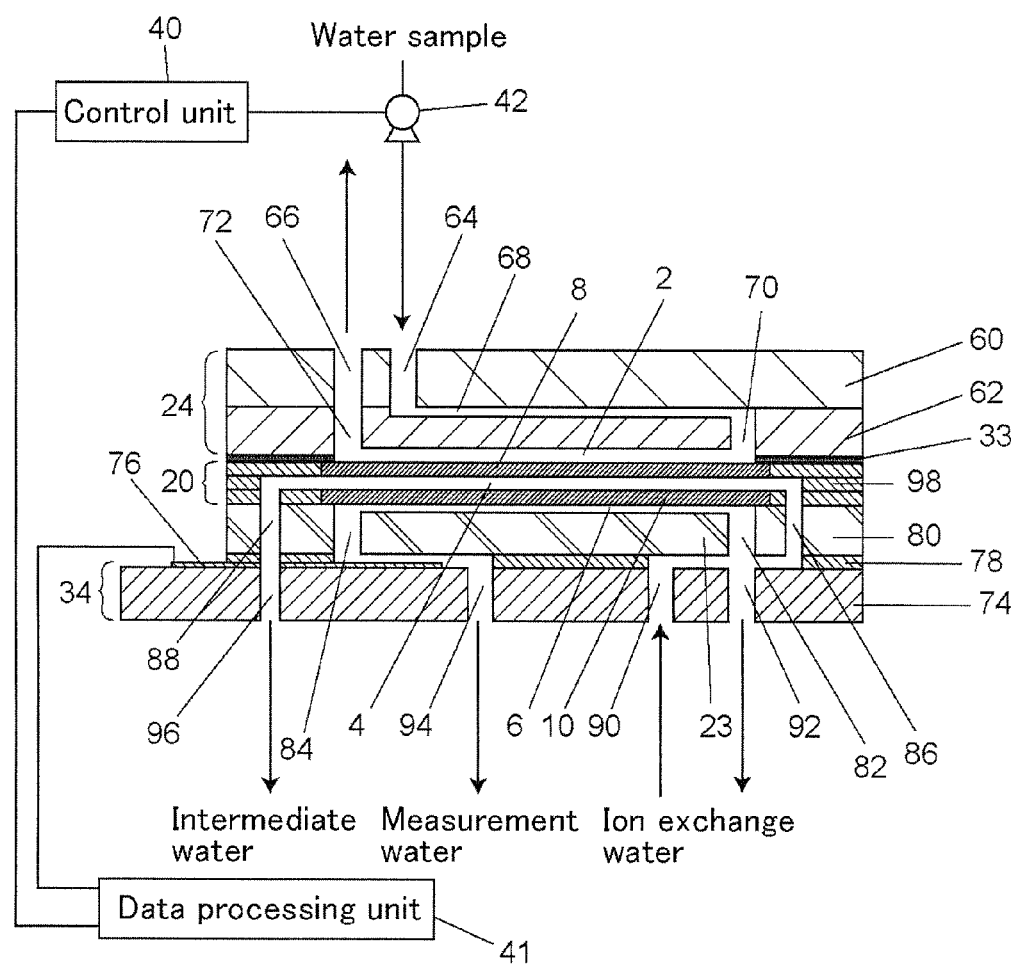
FIG. 1 is a schematic sectional view of one embodiment of a total organic carbon measuring instrument according to the present invention.

DESCRIPTION OF THE REFERENCE NUMERALS 2 water sample channel
4 intermediate water channel
6 measurement water channel
8,10 gas-permeable membrane
20 carbon dioxide separation part
24 organic substance oxidation part
34 conductivity measuring part
40 control unit
41 data processing unit
42 liquid feeding device
64 water sample inlet
66 water sample outlet

DETAILED DESCRIPTION OF THE INVENTION

Hereinbelow, an embodiment of the present invention will be described.

FIG. 1 is a schematic sectional view of one exmaple of a total organic carbon measuring instrument according to the present invention. The total organic carbon measuring instrument includes a measuring unit, a liquid feeding device 42 for feeding a water sample to the measuring unit, a control unit 40 for controlling the liquid feeding device 42, and a data processing unit 41 for determining TOC based on conductivity. The measuring unit is obtained by integrating an organic substance oxidation part 24, a carbon dioxide separation part 20, and a conductivity measuring part 34. It is to be noted that when it is necessary to differentiate between the top surface and the back surface of each substrate, the upper surface and the lower surface thereof shown in FIG. 1 will be referred to as "top surface" and "back surface", respectively.

The organic oxidation part 24 is constituted from a substrate 60 on which UV light is incident and a substrate 62 bonded to the substrate 60. As the substrate 60, a quartz substrate allowing UV light to pass through it is used to decompose organic substances by UV light emitted from above. The substrate 60 has a UV light incident portion on which UV light is incident. The substrate 60 also has a through hole 64 serving as a water sample inlet and a through hole 66 serving as a water sample outlet. The substrate 62 is also formed from a quartz substrate. The substrate 62 has an oxidation channel 68 provided in the top surface thereof so that one end of the oxidation channel 68 is located at a position corresponding to the water sample inlet 64. The substrate 62 has a water sample channel 2 provided in the back surface thereof so that one end of the water sample channel 2 is located at a position corresponding to the water sample outlet 66. Further, the substrate 62 has a through hole 70 through which the other end of the oxidation channel 68 and the other end of the water sample channel 2 are connected to each other and a through hole 72 through which the one end of the water sample channel 2 and the water sample outlet 66 are connected to each other. A light-blocking metal film 33 is provided on the back surface of the substrate 62, that is, on one surface of the substrate 62 opposite to the other surface thereof being in contact with the substrate 60. The light-blocking metal film 33 defines a region irradiated with UV light. An example of the light-blocking metal film 33 includes a Pt/Ti film (which is obtained by forming a platinum film on a titanium film provided as a bonding layer) having a thickness of 0.05 μm or more.

The sizes of the oxidation channel 68 and the water sample channel 2 are not particularly limited. For example, the oxidation channel 68 and the water sample channel 2 may be formed using a processing technique such as wet etching or dry etching so as to have a width of about 1 mm, a depth of about 0.2 mm and a length of about 200 mm. The through holes 64, 66, and 70 can be formed using a processing technique such as sandblasting. The substrate 60 and the substrate 62 can be bonded together using hydrogen fluoride.

The conductivity measuring part 34 is formed by bonding an electrode pattern 76 formed from a Pt/Ti film on a quartz substrate 74 to the back surface of a quartz substrate 80 with a film 78, part of which has been removed to form a flow channel pattern, being interposed therebetween.

Examples of the film 78 include an adhesive fluorine resin film (e.g., a 100 μm-thick film made of Neoflon EFEP ("Neoflon" is a trademark of Daikin Industries, Ltd.)) and a PDMS (polydimethylsiloxane) film (e.g., a 100 μm-thick film made of Sylgard 184 ("Sylgard" is a trademark of DOW CORNING)). On the electrode pattern 76, a flow channel for allowing measurement water to flow through it is provided by the film 78.

The electrode pattern 76 can be formed by patterning a sputtered Pt/Ti film by photolithography and etching used in the fields of semiconductor manufacturing and microfabrication. However, a method for forming the electrode pattern 76 is not particularly limited. Further, a film for forming a flow channel on the electrode pattern 76 is not limited to a Neoflon film or a PDMS film. For example, an adhesive organic film or a thin film coated with an adhesive may be used to form a flow channel on the electrode pattern 76. Therefore, a method for forming a flow channel on the electrode pattern 76 is not limited to a method using a Neoflon film or a PDMS film.

The quartz substrate 80 has a measurement water channel 6 formed in the top surface thereof. The quartz substrate 80 has a measurement water branch channel 82 connected to one end of the measurement water channel 6 and a through hole 84 for connecting the other end of the measurement water channel 6 to the flow channel provided on the electrode pattern 76 of the conductivity measuring part 34. Further, the quartz substrate 80 has a through hole 86 serving as an intermediate water branch channel for guiding intermediate water and a through hole 88 serving as an intermediate water outlet for discharging intermediate water. The thickness of the quartz substrate 80 is not particularly limited. For example, the quartz substrate 80 having a thickness of 1 mm is used.

The quartz substrate 74 has a through hole 90 serving as an ion exchange water inlet for supplying ion exchange water as deionized water and a through hole 92 serving as an ion exchange water outlet for discharging excess ion exchange water. The ion exchange water inlet 90 is connected to the measurement water branch channel 82, the intermediate water branch channel 86, and the ion exchange water outlet 92 through the flow channel formed by the PDMS film 78 interposed between the substrates 74 and 80.

The quartz substrate 74 has a through hole 94 serving as a measurement water outlet for discharging measurement water from the flow channel provided on the electrode pattern 76 of the conductivity measuring part 34 after conductivity detection and a through hole 96 connected to the through hole 88, which is provided as an intermediate water outlet in the quartz substrate 80, to serve as an intermediate water outlet for discharging intermediate water. The carbon dioxide separation part 20 is provided by bonding together the back surface of the substrate 62 constituting the organic substance oxidation part 24 and the top surface of the substrate 80 constituting the conductivity measuring part 34 with two gas-permeable membranes 8 and 10 being interposed therebetween. The gas-permeable membranes 8 and 10 constitute the carbon dioxide separation part 20.

Further, a PDMS film 98 is interposed between the gas-permeable membranes 8 and 10 to create a clearance corresponding to the thickness of the PDMS film 98. The PDMS film 98 has a pattern corresponding to an intermediate water channel 4. The intermediate water channel 4 is formed so that one end thereof is connected to the intermediate water branch channel 86 provided in the quartz substrate 80 to guide intermediate water, and the other end thereof is connected to the through hole 88 serving as an intermediate water outlet.

Intermediate water flowing through the intermediate water channel 4 has a pH higher than that of a water sample but within a neutral range. At least part of the intermediate water channel 4 is parallel with the water sample channel 2 and the measurement water channel 6 so as to come into contact with the water sample channel 2 and the measurement water channel 6 with the gas-permeable membranes 8 and 10.

The interface between the gas-permeable membrane 8 and the substrate 62 is sealed with a film such as a PDMS film because the water sample channel 2 is provided between the gas-permeable membrane 8 and the substrate 62. Also, the interface between the gas-permeable membrane 10 and the substrate 80 is sealed with a film such as a PDMS film because the measurement water channel 6 is provided between the gas-permeable membrane 10 and the substrate 80.

The gas-permeable membranes 8 and 10 are not particularly limited as long as they do not have carbon dioxide selectivity. Examples of such gas-permeable membranes 8 and 10 include porous fluorine resin membranes (e.g., a 30 μm-thick Poreflon membrane manufactured by Sumitomo Electric Fine Polymer, Inc.).

In the case of the total organic carbon measuring instrument according to this embodiment, a water sample is introduced through the water sample inlet 64 provided in the substrate 60, flows through the oxidation channel 68 and the water sample channel 2, and is then discharged through the water sample outlet 66. More specifically, the water sample introduced into the organic substance oxidation part 24 through the water sample inlet 64 is oxidized by irradiation with UV light, and is then brought into contact with intermediate water separated by the gas-permeable membrane 8 of the carbon dioxide separation part 20 so that gas components such as carbon dioxide are transferred into the intermediate water.

Ion exchange water is produced by an external unit and is then introduced through the ion exchange water inlet 90. Most of the ion exchange water introduced through the ion exchange water inlet 90 is directly discharged through the ion exchange water outlet 92, but only a necessary amount of the ion exchange water is supplied to the measurement water channel 6 and the intermediate water channal 4 through the measurement water branch channel 82 and the intermediate water branch channel 86, respectively.

The intermediate water channel 4 is in contact with both the gas-permeable membrane 8 to be brought into contact with the water sample and the gas-permeable membrane 10 to be brought into contact with the measurement water, and therefore, gas components transferred from the water sample into the intermediate water are distributed to the measurement water while keeping equilibriums with their respective ions generated in the intermediate water, and then the intermediate water is discharged to the outside through the intermediate water outlets 88 and 96. On the other hand, the measurement water flowing through the measurement water channel 6 receives the gas components, flows through the flow channel provided on the electrode pattern 76, and is then discharged through the measurement water outlet 94.

The feeding of the water sample is controlled by operating the liquid feeding device 42 and the control unit 40. More specifically, the feeding of the water sample is stopped during oxidation of organic substances, and is performed only when the water sample is moved to the carbon dioxide separation part 20 through the organic substance oxidation part. The data processing unit 41 determines the concentration of total organic carbon based on conductivity measured when the water sample irradiated with UV light of which relative intensity is equal to or higher than a certain value is flowing through the carbon dioxide separation part 20.

In the case of the total organic carbon measuring instrument according to this embodiment, for example, a pen-type low-pressure mercury lamp (L937-02) manufactured by Hamamatsu Photonics K. K. can be used as a UV lamp emitting UV light with which the water sample is irradiated. The light intensity distribution of this lamp is shown in FIG. 2.

Figure 2:
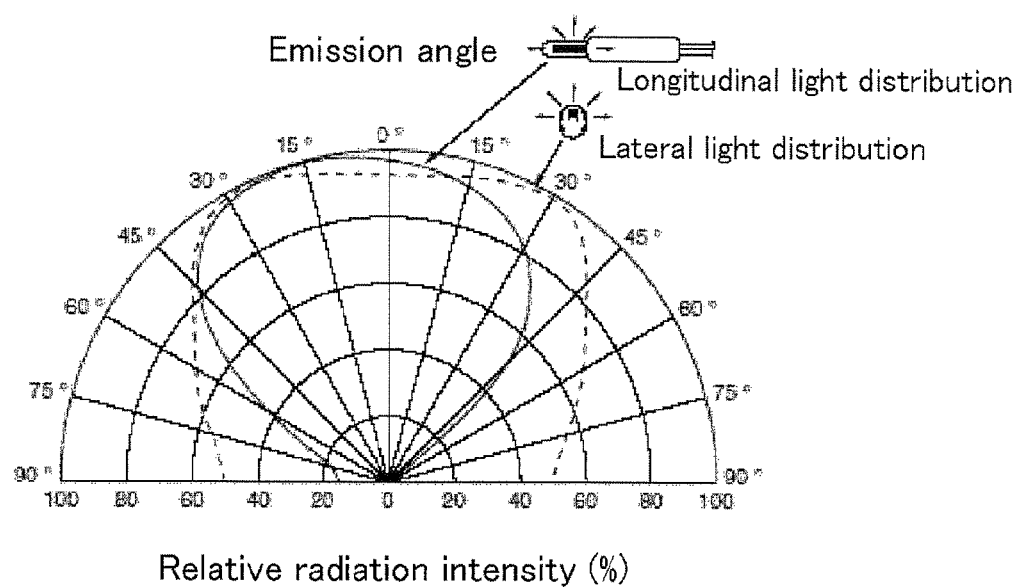
FIG. 2 is a schematic sectional view of another example of a carbon dioxide separation part.

In FIG. 2, a curve shown by the solid line indicates longitudinal light distribution, and a curve shown by the dashed line indicates lateral light distribution. The term "longitudinal light distribution" means the distribution of light emitted from the tip of the pen-type lamp, and the term "lateral light distribution" means the distribution of light emitted from the lateral side of the pen-type lamp. The angles indicated along a circular arc are emission angles of UV light emitted from the lamp placed at the center of the circular arc, and the distance from the center represents relative radiation intensity.

As can be seen from FIG. 2, the intensity distribution of UV light emitted from the pen-type low-pressure mercury lamp is not uniform. More specifically, the relative intensity of UV light emitted from the lamp placed at the center of the circular arc measured at an emission angle of 30° or less is 90% or more, and the relative intensity of UV light emitted from the lamp measured at an emission angle of 45° or more is 80% or less.

Since the intensity of UV light attenuates as the distance between the pen-type low-pressure mercury lamp and an irradiated subject increases, the distance between the lamp and an irradiated subject is preferably as small as possible. However, the area of a region irradiated with high-intensity UV light decreases as the distance between the lamp and an irradiated subject decreases. Therefore, the inventors of the present invention have studied the relationship between the flow channel pattern of an irradiated subject and UV light intensity.

Figure 3A:
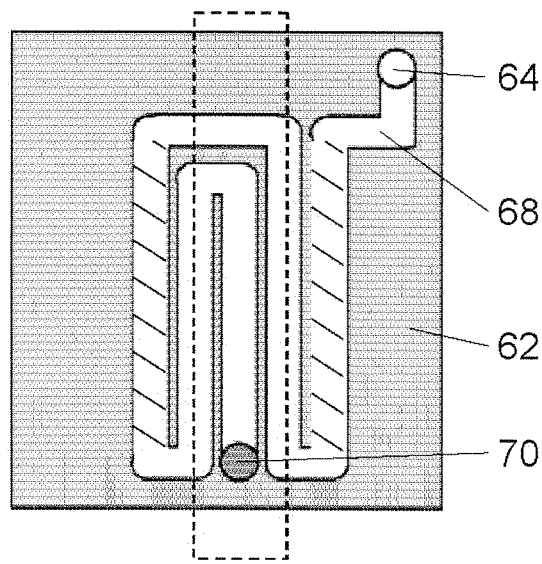
FIG. 3A is a plan view showing an example of an oxidation channel having an unoptimized flow channel pattern.
Figure 3B:
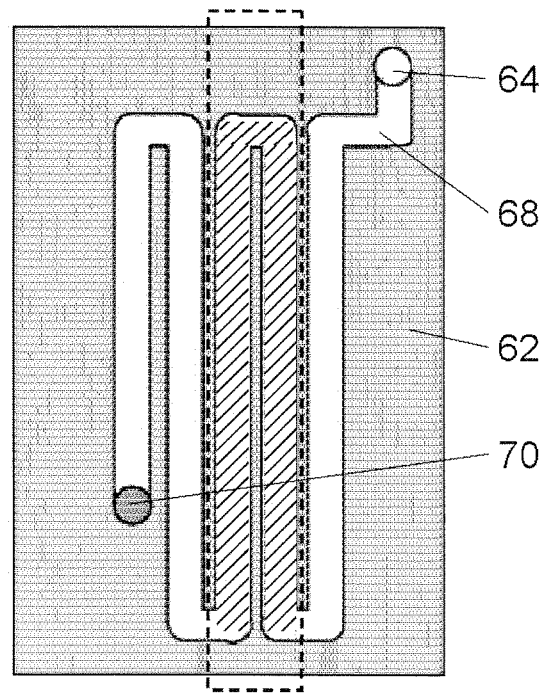
FIG. 3B is a plan view showing an example of an oxidation channel having an optimized flow channel pattern.

FIG. 3A is a plan view of an example of the oxidation channel 68 having an unoptimized flow channel pattern, and FIG. 3B is a plan view of an example of the oxidation channel 68 having an optimized flow channel pattern. In each of FIGS. 3A and 3B, a region surrounded by the dashed line indicates a region in which the pen-type low-pressure mercury lamp is placed. In the case of the oxidation channel 68 shown in FIG. 3A, the channel pattern complicatedly meanders from the water sample inlet 64 to the through hole 70. In FIG. 3A, the diagonally shaded areas represent regions in which the relative radiation intensity of UV light is 80% or less. On the other hand, in the case of the oxidation channel 68 shown in FIG. 3B, the channel pattern meanders from the water sample inlet 64 to the through hole 70 along the mercury lamp so as to be parallel with the mercury lamp. In FIG. 3B, the diagonally shaded area represents a region in which the relative radiation intensity of UV light is 90% or more.

As can be seen from FIGS. 3A and 3B, the intensity distribution of UV light with which the water sample is irradiated is not uniform, and therefore, there is a case where the concentration of carbon dioxide generated by oxidation in the water sample varies depending on the time elapsed since the start of feeding of the water sample to the carbon dioxide separation part.

Figure 4A:
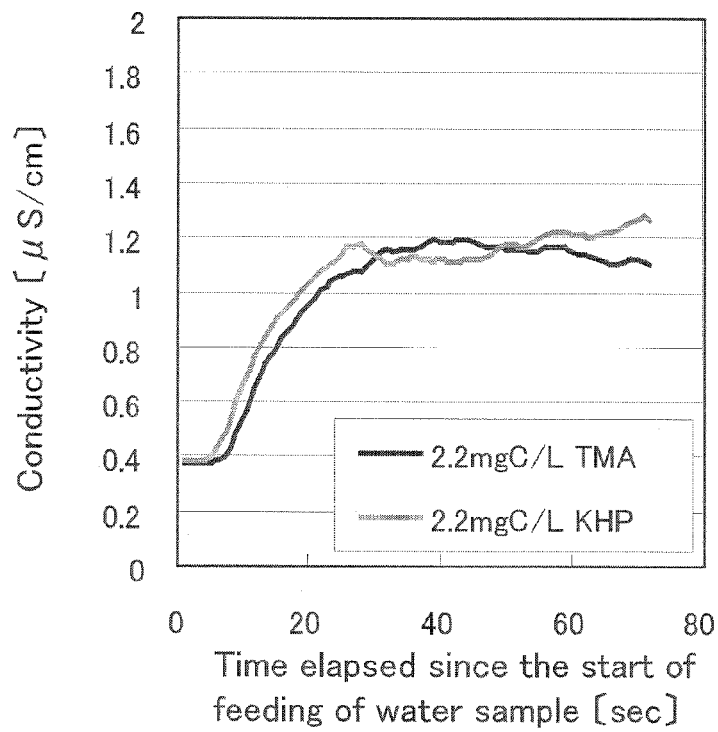
FIG. 4A is a graph showing the result of experiment performed using the flow channel pattern shown in FIG. 3A.
Figure 4B:
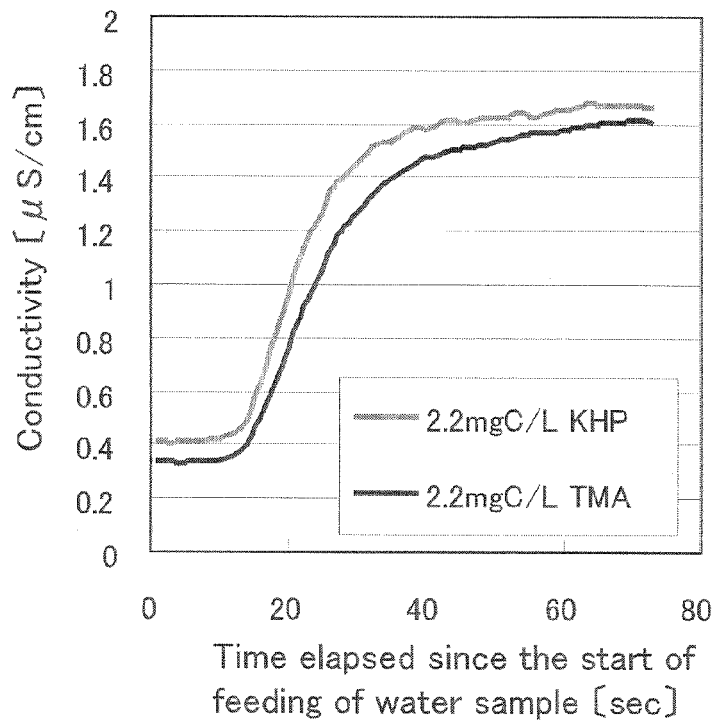
FIG. 4B is a graph showing the result of experiment performed using the flow channel pattern shown in FIG. 3B.

FIGS. 4A and 4B show the results of conductivity detection using the oxidation channels shown in FIGS. 3A and 3B, respectively. The capacity of the oxidation channel shown in FIG. 3A is about 130 μL, and the water sample introduced through the water sample inlet 64 is fed to the water sample channel 2 at a flow rate of 100 μL/min after the completion of oxidation of organic substances. In this case, part of the water sample irradiated with UV light of which relative radiation intensity is 80% or less arrives at the water sample channel 2 after a lapse of about 40 to 70 seconds. On the other hand, the capacity of the oxidation channel shown in FIG. 3B is about 200 μL, and a water sample introduced through the water sample inlet 64 is fed to the water sample channel 2 at a flow rate of 100 μL/min after the completion of oxidation of organic substances. In this case, part of the water sample irradiated with UV light of which relative radiation intensity is 90% or more arrives at the water sample channel 2 after a lapse of about 30 to 90 seconds.

As described above, FIG. 4A is a graph showing the result of experiment performed using the instrument shown in FIG. 1 having the flow channel pattern shown in FIG. 3A, and FIG. 4B is a graph showing the result of experiment performed using the instrument shown in FIG. 1 having the flow channel pattern shown in FIG. 3B. In these experiments, an aqueous potassium hydrogen phthalate solution (hereinafter, simply referred to as "KHP") which is easily decomposed by oxidation and an aqueous trimethylamine hydrochloride solution (hereinafter, simply referred to as "TMA") which is not easily decomposed by oxidation were used as water samples. Each of these two water samples had a concentration of 2.2 mgC/L. The acquisition of conductivity was performed after a lapse of about 60 seconds since the start of feeding of the water sample. This is because the conductivity of KHP is preferably as stable as possible. The acquired conductivity was converted into TOC using a calibration curve.

As can be seen from FIG. 4A, in the case of KHP, the conductivity is increased for about 60 seconds after the start of feeding of KHP. On the other hand, in the case of TMA, the conductivity reaches its peak after a lapse of about 40 seconds since the start of feeding of TMA, and therefore, the conductivity measured after a lapse of about 60 seconds since the start of feeding of TMA is lower than its peak value. Therefore, in a case where the conductivity measured after a lapse of 60 seconds since the start of feeding of TMA is converted to TOC, the TOC of TMA lower than its true value is obtained, thus resulting in an error. It can be estimated that this is due to the following reasons: KHP can be decomposed even when the relative radiation intensity of UV light with which KHP is irradiated is as low as 80% or less, whereas TMA is fed to the carbon dioxide separation part 20 without being decomposed.

On the other hand, the flow channel pattern shown in FIG. 3B is designed so that part of the water sample irradiated with UV light of which relative radiation intensity is 90% or more can be sufficiently fed to the carbon dioxide separation part 20 after a lapse of 60 seconds since the start of feeding of the water sample. Therefore, as shown in FIG. 4B, in both cases of KHP and TMA, the conductivity is not decreased even after a lapse of about 60 seconds since the start of feeding of the water sample. In this case, the TOC of TMA is a true value.

Further, in the case of using the flow channel pattern shown in FIG. 3B, part of the water sample irradiated with UV light of which relative radiation intensity is 90% or less arrives at the carbon dioxide separation part 20 after a lapse of 0 second since the start of feeding of the water sample and flows through the carbon dioxide separation part 20 for 30 seconds. This is necessary for the following reasons. When a water sample is transferred from the organic substance oxidation part to the carbon dioxide separation part, carbon dioxide contained in the water sample is diffused into the dead volume of the carbon dioxide separation part so that the concentration of carbon dioxide attenuates in the carbon dioxide separation part. This causes a phenomenon in which the concentration of carbon dioxide measured by the conductivity measuring part is lowered. Therefore, in order to prevent the lowering of the concentration of carbon dioxide measured by the detection unit as much as possible, a water sample of which organic substances are decomposed by oxidation to some extent is fed to the carbon dioxide separation part just before the detection of conductivity to increase the concentration of carbon dioxide in the dead volume of the carbon dioxide separation part. This makes it possible to prevent the lowering of detection sensitivity.

As has been described above, according to the present invention, the control unit 40 stops the feeding of a water sample during oxidation of organic substances and performs the feeding of the water sample only when the water sample is moved to the organic substance oxidation part and the carbon dioxide separation part, and the data processing unit 42 determines the concentration of total organic carbon based on conductivity measured when the water sample irradiated with UV light of which relative intensity is equal to or higher than a certain value is flowing through the carbon dioxide separation part. Therefore, it is possible to reduce the consumption of the water sample and accurately measure the TOC content of the water sample.

Further, as described above, in order to reduce the amount of the water sample to be fed to the carbon dioxide separation part as much as possible also at times other than the time of measurement, the dead volume of the carbon dioxide separation part 20 should be reduced as much as possible. The dead volume of the carbon dioxide separation part 20 is mainly due to a porous fluorine resin membrane (gas-permeable membranes 8 and 10), and therefore can be reduced by decreasing the volume of gas contained in the porous fluorine resin membrane as much as possible.

One method for decreasing the volume of gas contained in a porous fluorine resin membrane is to reduce the thickness of the membrane. However, the porous fluorine resin membrane needs to have a certain degree of thickness due to manufacturing reasons. Another method for decreasing the volume of gas contained in a porous fluorine resin membrane is to reduce the area of the porous fluorine resin membrane 8 as much as possible. Since the intermediate water channel 4 and the measurement water channel 6 are present under the porous fluorine resin membrane 8, the area of the porous fluorine resin membrane can be reduced by minimizing the area of contact between the porous fluorine resin membrane and the water sample channel 2, the intermediate water channel 4, or the measurement water channel 6.

A smaller depth of a flow channel for use in separating carbon dioxide makes the time required to transfer carbon dioxide by diffusion shorter (this is because according to a diffusion equation, the transfer time is proportional to the square of the distance) so that carbon dioxide is transferred into another pure water in a shorter time. This makes it possible to reduce the length of the flow channel. That is, by reducing the depth of a flow channel for use in separating carbon dioxide as much as possible, it is possible to reduce the length of the flow channel, which leads to a reduction in the area of the porous fluorine resin membrane.

Figure 5:
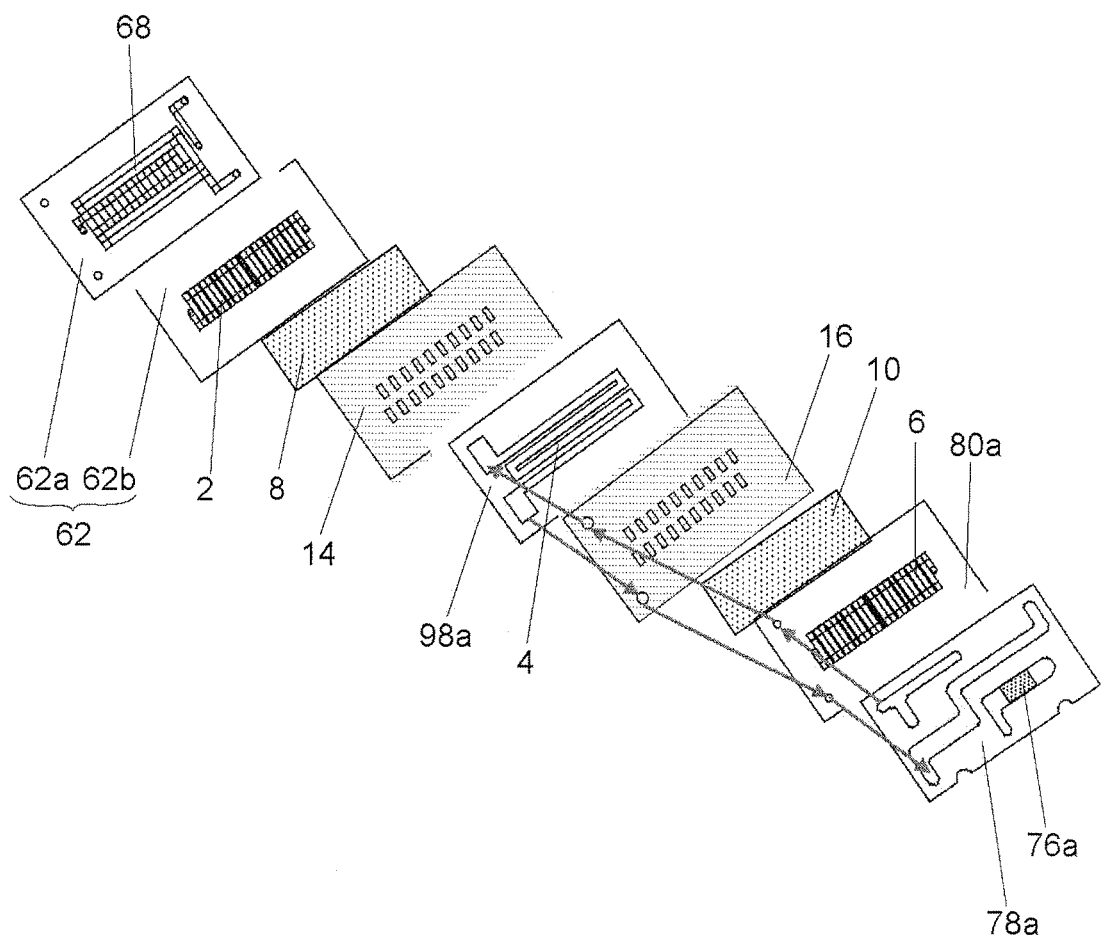
FIG. 5 is a schematic sectional view of another example of the carbon dioxide separation part.
Figure 6:
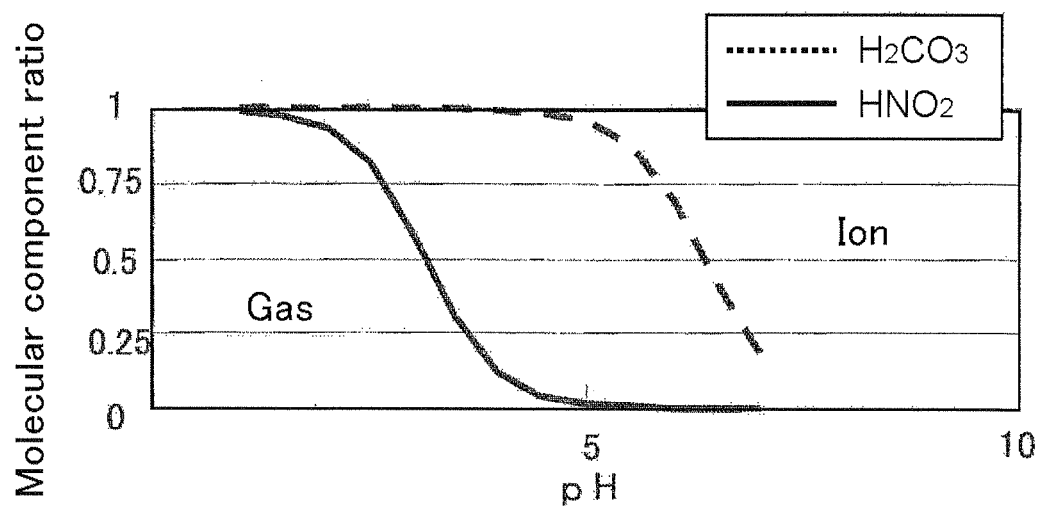
FIG. 6 is a graph showing molecular component ratio-versus-pH curves of nitrous acid and carbon dioxide.

FIG. 5 is an exploded perspective view of another embodiment of the total organic carbon measuring instrument according to the present invention. As in the case of the embodiment shown in FIG. 1, this embodiment shown in FIG. 5 is formed by integrating the organic substance oxidation part, the carbon dioxide separation part, and the conductivity measuring part. The oxidation channel 68 is formed as a groove having a depth of 0.6 mm in a top surface 62a of the quartz substrate 62, and the water sample channel 2 is formed as a groove having a thickness of 60 μm in a back surface 62b of the quartz substrate 62. The intermediate water channel 4 is formed as a through groove in a 100 μm-thick membrane 98a made of an adhesive fluorine resin (e. g., Neoflon EFEP "Neoflon" is a trademark of Daikin Industries Ltd.)), and the measurement water channel 6 is formed as a groove having a depth of 60 μm in a surface 80a of the quartz substrate 80 (see FIG. 1) opposed to the gas-permeable membrane 10. The oxidation channel 68, the water sample channel 2, the intermediate water channel 4, and the measurement water channel 6 have a meandering shape to increase their flow channel lengths. These channels 2, 6, and 68 can be formed by, for example, sandblasting.

The conductivity measuring part has two electrode patterns. One of the electrode patterns is provided on a surface of the substrate 80 opposite to the surface 80a at a position corresponding to a position indicated by the reference numeral 76a, and the other electrode pattern is provided on a surface of the quartz substrate 74 (see FIG. 1) opposed to the substrate 80 at a position corresponding to a position indicated by the reference numeral 76a. A flow channel through which the measurement water flows is formed by cutting a flow channel pattern out of a 100 μm-thick membrane 78a made of an adhesive fluorine resin (e.g., Neoflon EFEP ("Neoflon" is a trademark of Daikin Industries Ltd.)) to be interposed between the substrates 80 and 74.

A shielding membrane 14 having openings is provided between the intermediate water channel 4 and the water sample channel 2 to adjust the area of contact between the water sample and the intermediate water. Further, a shielding membrane 16 having openings is provided between the intermediate water channel 4 and the measurement water channel 6 to adjust the area of contact between the intermediate water and the measurement water. An example of the shielding membranes 14 and 16 includes a 25 μm-thick membrane made of an adhesive fluorine resin (e.g., Neoflon EFEP (("Neoflon" is a trademark of Daikin Industries Ltd.)). An example of the gas-permeable membranes 8 and 10 includes a 30 μm-thick porous fluorine resin member (e.g., Poreflon ("Poreflon" is a trademark of Daikin Industries Ltd.).

The total organic carbon measuring instrument shown in FIG. 5 is formed by laminating the above-described quartz substrate 62, gas-permeable membrane 8, shielding membrane 14, adhesive fluorine resin membrane 98a, shielding membrane 16, gas-permeable membrane 10, quartz substrate 80a, electrode pattern 76a, and adhesive fluorine resin membrane 78a in this order from top to bottom, sandwiching them between a substrate as an uppermost layer corresponding to the quartz substrate 60 shown in FIG. 1 and a substrate as a lowermost layer corresponding to the quartz substrate 74 shown in FIG. 1, and bonding them together for integration.

The invention claimed is:

1. A total organic carbon measuring method using an instrument, the instrument comprising:
 a measuring unit having an organic substance oxidation part for oxidizing organic substances contained in a supplied water sample to carbon dioxide by irradiation with UV light, a carbon dioxide separation part having a water sample channel through which a water sample transferred from the organic substance oxidation part flows and a measurement water channel through which measurement water constituted from deionized water flows, the carbon dioxide separation part being formed by integrating the water sample channel and the measurement water channel being in contact with each other gas-permeably and laminated in this order from top to bottom, and a conductivity measuring part for measuring a conductivity of the measurement water transferred from the carbon dioxide separation part, the measuring unit being formed by laminating the organic substance oxidation part, the carbon dioxide separation part, and the conductivity measuring part in this order from top to bottom,
 wherein an intensity distribution of the UV light for irradiating the water sample is non-uniform in a flow channel of the organic substance oxidation part resulting in a non-uniform distribution of the carbon dioxide in the water sample in the flow channel irradiated by the UV light;

a control unit for controlling the operation of liquid delivery in the measuring unit; and a data processing unit for determining a concentration of total organic carbon from a conductivity of measurement water, the method comprising the steps of:

controlling step by the control unit to stop feeding the water sample during oxidation of organic substances and to perform feeding the water sample when the water sample is moved to the carbon dioxide separation part through the organic substance oxidation part, wherein the water sample irradiated with the UV light has a portion irradiated with the UV light of which relative intensity is equal to or higher than a certain value and the other portion irradiated with the UV light of which relative intensity is lower than the certain value by the oxidation during the stop feeding the water sample, and data processing step by the data processing unit to determine the concentration of total organic carbon based on the conductivity measured when the portion of the water sample irradiated with the UV light of which relative intensity is equal to or higher than the certain value is flowing through the carbon dioxide separation unit.

2. The total organic carbon measuring method according to claim 1, wherein the carbon dioxide separation part has, between the water sample channel and the measurement water Channel, an intermediate water channel in which intermediate water having a pH higher than that of the water sample flowing through the water sample channel but within a neutral range is present, and wherein the water sample channel and the intermediate water channel are in contact with each other with a gas-permeable membrane being interposed therebetween, and the intermediate water channel and the measurement water Channel are in contact with each other with another gas-permeable membrane being interposed therebetween, and wherein the water sample channel, the intermediate water channel, and the measurement water channel are laminated in this order from top to bottom and integrated.

3. The total organic carbon measuring method according to claim 1, wherein part of the water sample channel being in contact with the gas-permeable membrane meanders to have an increased flow channel length.

4. The total organic carbon measuring method according to claim 1, wherein part of the measurement water channel being in contact with the gas-permeable membrane meanders to have an increased flow channel length.

5. The total organic carbon measuring method according to claim 2, wherein part of the intermediate water channel being in contact with the gas-permeable membranes meanders to have an increased flow channel length.

6. The total organic carbon measuring method according to claim 2, wherein a buffer solution having, a pH within a neutral range is used as the intermediate water.

7. The total Organic carbon measuring method according to claim 3, wherein part of the measurement water channel being in contact with the gas-permeable membrane meanders to have an increased flow channel length.

8. The total organic carbon measuring method according to claim 2, wherein part of the water sample channel being in contact with the gas-permeable membrane meanders to have an increased flow channel length, wherein part of the measurement water channel being in contact with the gas-permeable membrane meanders to have an increased flow channel length, and wherein part of the intermediate water channel being in contact with the gas-permeable membranes meanders to have an increased flow channel length.

\* \* \* \* \*